Aug. 21, 1973 M. B. WAKEFIELD Plant Pat. 3,387
DOGWOOD TREE
Filed Jan. 20, 1972
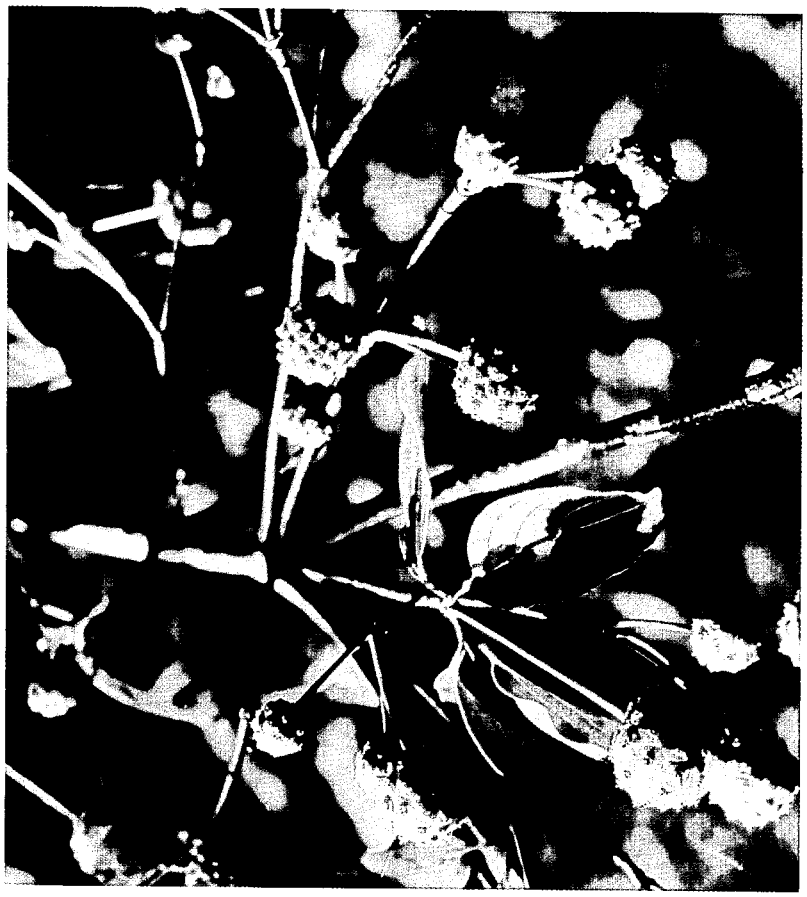
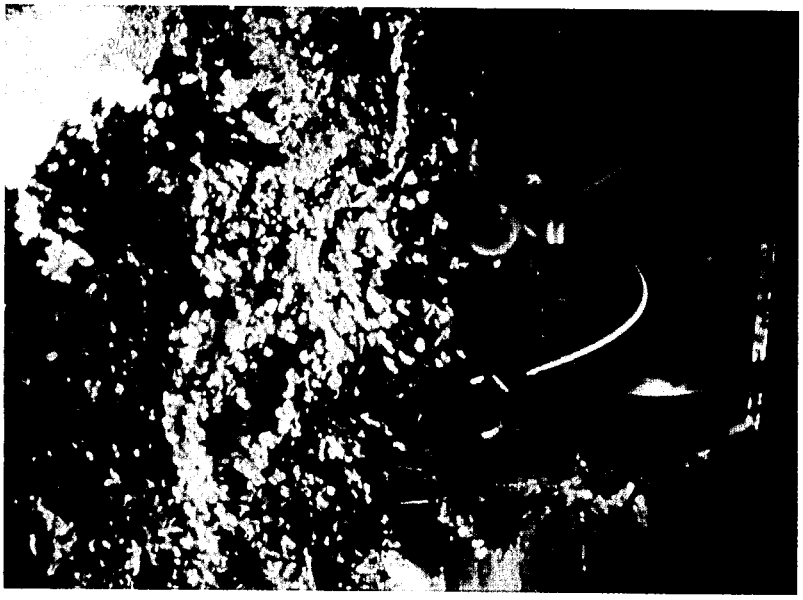

United States Patent Office

Plant Pat. 3,387
Patented Aug. 21, 1973

3,387

DOGWOOD TREE

Mary B. Wakefield, 1465 Brush Hill Road,
Milton, Mass. 02186

Filed Jan. 20, 1972, Ser. No. 219,582
Int. Cl. A01h 5/12
U.S. Cl. Plt.—51 1 Claim The present invention relates to a new and distinct variety of dogwood tree of the Japanese dogwood type botanically known as *Cornus kousa*, which was originated by me from seed which was initially processed and planted by me indoors, and then set out as a young seedling plant in my outdoor experimental nursery which I maintain on my home property located at Milton, Mass.

At the time I acquired the original seed from which I developed this new dogwood variety, I was attending classes on plant propagation as conducted at the Arnold Arboretum which is near my home in Milton, Mass. My interest in plant propagation and experimentation led me to seek and receive permission to obtain seeds of various plants, including dogwoods, being grown at the Arnold Arboretum. This particular dogwood seed was one of many which were collected by me from a dogwood tree specimen of the kousa type but of uncertain parentage, which had attracted my attention at the Arboretum aforementioned because of the exceptionally large size of the fruit borne thereby. In a few years after setting out and observing this seedling in my nursery, I was particularly impressed by its unusually graceful habit and delicate form, and expecially by its unusually heavy floriferousness and prolonged, heavy and exceptionally showy fruiting habit.

Continued observations of the original seedling and progeny thereof derived from rooted cuttings which I developed therefrom and planted in my nursery, have convinced me and the experts at the Arnold Arboretum that my new seedling represents a new and distinct dogwood variety which is definitely distinguished from its parent variety, as well as from all other dogwood varieties known to us, as evidenced by the following unique combination of principal characteristics which are outstanding therein:

(1) A relatively small and dainty tree habit, with a flat-topped but generally upright form of slender, graceful sweeping branches;

(2) An exceptionally heavy floriferousness, with pure white blooms being borne mostly in triple clusters and occasionally in double clusters, or sometimes singly, thereby giving the tree a striking and massive pure white color effect like a mantle of snow;

(3) An unusually heavy, prolonged and showy fruiting habit, with the fruit being borne mostly in loose triple clusters which ripen in succession over a period of 6 weeks or more (well into November in Massachusetts) and which give the tree a striking bright red overall color as the fruit matures;

(4) Excellent hardiness to at least −20° F. without injury; and (5) Especial suitability for foreground accent of massed plantings of trees and shrubs, as well as for use near buildings and for lawn, courtyard and garden plantings and the like.

The accompanying drawing shows a typical tree specimen of my new dogwood variety during the blooming season and depicting the distinctive mass effect of its white blooms which almost completely cover the tree, and also show the typical cluster habit of the fruit during the fruiting season.

The following is a detailed description of my new dogwood variety, with color terminology in accordance with the Royal Horticultural Colour Chart, published by the Royal Horticultural Society of London, except where general color terms of ordinary dictionary significance are obvious:

Parentage: Seedling of an unnamed and unpatented variety of the species *C. kousa* of uncertain origin and parentage.

Propagation: Holds its distinguishing characteristics through succeeding propagations by rooted cuttings.

Locality where grown and observed: Milton, Mass.

Tree: Small; dainty; generally upright; low-growing (up to about 8 feet tall); somewhat flat-topped.

*Trunk.*—Slender; smooth.

*Branches.*—Slender; with graceful sweeping habit (branches at one side of tree extend laterally, then upwardly and then downward at tips, while those at opposite side of tree extend laterally, then downwardly and then upward at tips).

*Leaves.*—Among leaves which drop latest in fall season. Quantity—abundant. Size—length—from about 2½ inches to 3½ inches. Width—from about 1 inch to 2 inches. Shape—elliptic ovate, with cordate tip. Color—Dark green blend of colors 133A and 136A; color turns wine red in fall season (usually in November at Milton, Mass.), as typical of the species. Margin—Serrate. Petiole—short.

Flower buds:

*Hardiness.*—Excellent; have withstood temperatures of −20° F. without injury.

*Size.*—Length—from about ¼ inch to 5/16 inch. Width—from about ¼ inch to 5/16 inch.

*Shape.*—Distinctly 3-lobed.

*Color.*—Near colors 199C or 199D, with whitish pubescence.

Flowers (inflorescence):

*Dates of first and full bloom.*—About June 1 and June 15, respectively, at Milton, Mass.

*Quantity.*—Unusually abundant and showy.

*Borne.*—Mostly in clusters of 3, with occasional clusters of 2 or sometimes singly.

*Size.*—Variable according to number originating from same twig; usually from about 1½ inches to 3 inches in diameter.

*Petalage.*—Normal; 4 bracts.

*Color.*—Normal for species; pure white, with mass effect giving appearance of a mantle of snow almost entirely covering tree.

Fruit:

*Quantity.*—Exceptionally abundant and showy.

*Borne.*—Mostly in loose triple clusters, with some standing up from twigs, others held straight out, and some hanging downward from ends of twigs; but do not touch each other.

*Size.*—Variable; about ½ inch in diameter or a little more when borne in triple clusters, to about 1 inch in diameter when borne singly.

*Color.*—Changes from green to yellow to clear bright red when mature; color of different fruit does not change at same rate, so red color effect is successive and is unusually prolonged for about 6 weeks, extending well into November at Milton, Mass.

General observations: The dainty and gracefully sweeping but generally upright habit of the tree of my new dogwood variety, combined with the abundant and showy habit of its clusters of pure white blooms which clothe the tree with a mass effect of a mantle of snow, and further combined with the cluster habit and prolonged and showy bright red mass color effect of the fruit, is unique in dogwood varieties and makes my new variety especially suitable for garden, park and foundation plantings, and particularly for lawn and courtyard plantings, where there has been a long need for hardy new ornamentals of relatively small size. It is of interest all year around, as observed both at close range and at a distance, and stands out in striking comparison with all other dogwood varieties.

I claim:

1. A new and distinct variety of dogwood tree of the Japanese dogwood type, substantially as herein shown and described, characterized particularly as to novelty by the unique combination of a relatively small and dainty tree habit, with a flat-topped but generally upright form of slender, gracefully sweeping branches, an exceptionally heavy floriferousness, with pure white blooms being borne mostly in triple clusters and occasionally in double clusters or sometimes singly, thereby giving the tree a striking and massive pure white color effect like a mantle of snow, an unusually heavy, prolonged and showy fruiting habit, with the fruit being borne mostly in loose triple clusters which ripen in succession over a period of 6 weeks or more (well into November in Massachusetts) and which give the tree a striking bright red overall color as the fruit matures, excellent hardiness to at least −20° F. without injury, and especial suitability for foreground accent of massed plantings of trees and shrubs, as well as for use near buildings and for lawn, courtyard and garden plantings and the like.

No references cited.

ROBERT E. BAGWILL, Primary Examiner